United States Patent [19]

Fuhge et al.

[11] Patent Number: 4,510,126
[45] Date of Patent: Apr. 9, 1985

[54] REAGENT FOR THE DETERMINATION OF RISTOCETIN COFACTOR (V.WILLEBRAND FACTOR)

[75] Inventors: Peter Fuhge, Lahntal; Konrad Braun, Ebsdorfergrund; Udo Becker, Munich, all of Fed. Rep. of Germany

[73] Assignee: Hoechst Aktiengesellschaft, Frankfurt, Fed. Rep. of Germany

[21] Appl. No.: 430,748

[22] Filed: Sep. 30, 1982

[30] Foreign Application Priority Data

Oct. 22, 1981 [DE] Fed. Rep. of Germany ....... 3141894

[51] Int. Cl.$^3$ .......................... G01N 1/00; G01N 1/30; G01N 33/48
[52] U.S. Cl. ........................................... 424/3; 424/2; 424/7.1; 436/10
[58] Field of Search .................... 424/2, 3, 7.1; 436/10

[56] References Cited

U.S. PATENT DOCUMENTS 4,287,087  9/1981  Brmhous et al. ...................... 424/2

OTHER PUBLICATIONS

Tullis, *Blood Cells and Plasma Proteins,* Academic Press NY, 1953, pp. 151–152.
Lillies, *Histopathologic Technic,* McGraw Hill, NY, 1965, pp. 350–352.

Primary Examiner—Robert J. Warden
Assistant Examiner—K. S. Moss
Attorney, Agent, or Firm—Curtis, Morris & Safford

[57] ABSTRACT

An agent for determining ristocetin cofactor (v.Willebrand factor) is described, which contains platelets which have been treated with a tanning agent, with a protease inhibitor and, optionally, with a dye-stuff, and ristocetin A.

4 Claims, No Drawings

REAGENT FOR THE DETERMINATION OF RISTOCETIN COFACTOR (V.WILLEBRAND FACTOR)

The invention relates to an agent for determining ristocetin cofactor, also denoted v. Willebrand factor or F VIII R:RCF. This contains platelets which have been treated with a tanning agent, with a protease inhibitor and, optionally, with a dyestuff, and ristocetin A.

Determination of the ristocetin cofactor (F VIII R:RCF) activity is suitable for the diagnosis of the v. Willebrand syndrome (WS). Known processes depend upon the fact that the antibiotic ristocetin A induces the aggregation of platelets in human platelet rich plasma, but not in the platelet rich plasma from subjects with the v. Willebrand syndrome.

According to the state of the art, ristocetin cofactor can be determined as follows:

Citrated human plasma is added to a suspension of washed human platelets, the aggregation of the platelets is induced by the addition of ristocetin and is measured using the change in transmission in a photometer with a device for measuring aggregations (aggregometer). The transmission increases due to the aggregation of the platelets. In order to obtain a reference curve, stepwise dilutions of pooled human plasma are used. The aggregation can be measured as an increase in the transmission in unit time and be plotted against the plasma dilution. The content of ristocetin cofactor in a patient's plasma can be read off from the reference curve.

The disadvantages of processes of this type are that they require experienced technical personnel, accurate working and a recorder which exactly reproduces the change in transmission on aggregation, since an error of one degree in the measurement of the slope can correspond to an error of 10% in the concentration of ristocetin cofactor.

In addition, it is very time-consuming to prepare the fresh suspensions of blood platelets having a constant number of platelets which are necessary for the process. These suspensions can only be kept for a limited period.

A further disadvantage of the process mentioned is the large test volume, which necessitates large amounts of costly ristocetin. Siince the concentration of ristocetin can only be varied within a narrow range, saving is only possible by decreasing the test volume. An agglutination test on test dishes, in the manner of a latex test, decreases the test volume to one tenth without affecting the sensitivity of the test. Fresh suspensions of platelets are not suitable for this purpose, since they already contain aggregates of platelets which bring about agglutination in the zero check.

Determination of the ristocetin cofactor has already been further simplified by using platelets treated with a tanning agent. Suspensions of blood platelets, which are active even after storage, particularly when they are freeze dried, are obtained by fixing with glutaraldehyde (German Offenlegungsschrift No. 2,546,166) or formalin (Allain et al., J. Lab. Clin. Med. (1975), 85, 318). However, when platelets which have been freeze dried in this manner are resuspended, increased platelet aggregates are then found which have an adverse effect on their use in an agglutination test, since the zero check again shows spontaneous agglutination. Even when platelets are freeze dried together with ristocetin, spontaneous aggregates form on resuspension, and these make it impossible for them to be used in an agglutination test.

It has now been found that the described disadvantages of the known processes are avoided by using a reagent which depends on the surprising finding that platelets treated with a protease inhibitor and a tanning agent known for fixing proteins can be freeze dried with ristocetin and auxiliaries and can be stored for a relatively long period at room temperature or even at 37° C. without losing their utility for determining ristocetin cofactor.

The invention relates to an agent for determining ristocetin cofactor (V. Willebrand factor; F VIII R:RCF), which contains platelets, which have been treated with a protease inhibitor and with a tanning agent known for fixing proteins and, optionally, with a dyestuff known for staining proteins, and ristocetin A.

The reagent according to the invention permits semi-quantitative determination of ristocetin cofactor by the agglutination method with only two pipetting steps (reagent and sample) and using only little ristocetin.

It has been found to be favorable to fix the platelets with a solution of a $C_1$–$C_4$-alkanaldehyde, preferably formaldehyde, or a $C_2$–$C_6$-dialdehyde, preferably glutaraldehyde, at a minimum concentration of 0.2% (w:v) for at least 2 hours at between 4° C. and 37° C. and additionally to treat them with a protease inhibitor, preferably diisopropyl fluorophosphate, at a minimum concentration of $10^{-6}$M. The platelets are optionally stained with a dyestuff known for staining proteins, particularly with one of the dyestuffs used in gel electrophoresis, such as coomassie blue, or with a reactive dye such as "Remazol Turquoise Blue EEAD 505" (=Colour Index Reactive Blue 21). The concentration of dyestuff for this purpose is at least 0.05 mg/ml and the staining time is 24 hours at most. Sufficient ristocetin A is added to the suspension containing $10^7$ to $10^{11}$ platelets per ml, so that it contains 0.2–10 mg/ml, preferably 2.5 mg/ml. The suspension is dried together with freeze-drying auxiliaries. 1 to 100 mg of one or more aminoacids, preferably glycine and sodium glutaminate, 2 to 30 mg of a sugar, preferably sucrose, and 0.5 to 10 mg of a protective colloid, preferably human albumin, are added as auxiliaries per ml of suspension.

The following example is intended to illustrate the invention in more detail:

1.3 l of platelet concentrate were suspended in 4 l of 0.15M phosphate buffer, pH 7.2, and the erythrocytes were removed by centrifugation. The washing and centrifugation was repeated twice and then the supernatant was adjusted to $3 \times 10^9$ platelets per ml. Under strict safety precautions (hood, gloves), diisopropyl fluorophosphate was added to a final concentration of $10^{-3}$M and the mixture was stirred at room temperature for 1 hour. After centrifugation, the supernatant was discarded and the precipitate was washed twice with phosphate buffer. The suspension ol platelets was adjusted to a concentration of 4% formaldehyde with a 35% strength formaldehyde solution and was stirred gently at 4° C. for 44 hours. The suspension was then dialyzed thoroughly against phosphate buffer. The concentration of platelets was adjusted to $3 \times 10^9$/ml and added to 1 l of a suspension of 2.5 g of ristocetin A, 10 g of sucrose, 10 g of glycine, 16.7 g of Na glutaminate and 2 g of human albumin. After freezing, the mixture was freeze dried. The number of platelets remained constant before and after freeze drying.

The platelets can also be stained after fixation, for example with "Remozol Turquoise Blue EEAD 505", which stains the platelets an intense blue and increases the sensitivity of the test.

The platelets can be stained by adding 0.25 mg/ml of said aforementioned "Remozol" dyestuff Remazol blue to the fixed and dialyzed suspension of platelets and stirring for 30 minutes. The mixture is then centrifuged and the precipitate is washed. After centrifugation, the platelets are further treated as were the unstained platelets.

In the case of this reagent, after reconstitution in $H_2O$, again no aggregates are observed.

DETERMINATION OF RISTOCETIN COFACTOR

For this, the freeze-dried material is reconstituted with 1 ml of water to give 1 ml of initial suspension, added to a geometric series of dilutions of pooled human plasma and the agglutination is evaluated.

Assay: 50 µl of plasma dilution and 50 µl of reagent are thoroughly mixed on a glass dish, shaken for 1 minute, allowed to stand for 1 minute and the titer is then read off.

Test of storage stability: after storing at 37° C. for 4 weeks, the same titer was found.

I claim:

1. An agent for determining ristocetin cofactor, which agent is a freeze-dried suspension of human platelets treated with diisopropyl fluorophosphate as a proteinase inhibitor and with a tanning agent selected from the group consisting of $C_1$–$C_4$-alkanaldehydes and $C_2$–$C_6$-dialdehydes.

2. An agent as in claim 1 wherein said platelets are additionally treated with Reactive Blue 21 dye.

3. An agent as in claim 2 wherein said freeze-dried suspension additionally comprises from 1 to 100 mg of at least one member selected from the group consisting of glycine and sodium glutaminate, from 2 to 30 mg of sucrose, and from 0.5 to 10 mg of human albumin as a protective colloid for about each $3(10^9)$ platelets.

4. An agent as in claim 1 wherein said freeze-dried suspension additionally comprises from 1 to 100 mg of at least one member selected from the group consisting of glycine and sodium glutaminate, from 2 to 30 mg of sucrose, and from 0.5 to 10 mg of human albumin as a protective colloid for about each $3(10^9)$ platelets.

* * * * *